United States Patent [19]
Dopatka et al.

[11] Patent Number: 5,138,551
[45] Date of Patent: Aug. 11, 1992

[54] PROCESS FOR IMPROVING THE ACCURACY AND REPRODUCIBILITY OF DATA MEASURED IN IMMUNOMETRIC TESTS

[75] Inventors: Hans-Detlef Dopatka, Marburg; Bernhard Giesendorf, Dornburg-Frickhofen, both of Fed. Rep. of Germany

[73] Assignee: Behringwerke Aktiengesellschaft, Marburg an der Lahn, Fed. Rep. of Germany

[21] Appl. No.: 451,255

[22] Filed: Dec. 15, 1989

[30] Foreign Application Priority Data

Dec. 17, 1988 [DE] Fed. Rep. of Germany ....... 3842580

[51] Int. Cl.⁵ .................................................. G06F 15/00
[52] U.S. Cl. ................................ 364/413.01; 435/7.9; 364/497
[58] Field of Search ............... 364/413.01, 413.11, 364/413.07, 413.09, 571.01, 571.02, 571.03, 571.04, 571.05, 571.06, 496, 497, 500; 436/51, 518; 435/7.9, 7.92, 7.1

[56] References Cited

U.S. PATENT DOCUMENTS

| Re. 28,803 | 5/1976 | Durkos et al. | 364/413.01 |
| 3,769,178 | 10/1973 | Rothermel, Jr. | 364/500 |
| 3,960,497 | 6/1976 | Acord | 364/571.01 |
| 4,211,614 | 7/1980 | Eppstein et al. | 364/497 |
| 4,884,213 | 11/1989 | Iwata et al. | 364/571.01 |

FOREIGN PATENT DOCUMENTS

60-154161 8/1985 Japan.
63-132166 6/1988 Japan.

OTHER PUBLICATIONS

B. Muller-Wiegand et al., Lab. Med. 10:65-70 (1986).
M. J. Bookbinder et al., Clin. Chem. 32/9:1734-1737 (1986).
W. Ehnert, Lab. Med. 3:A&B 75 (1979).
B. W. Stemshorn et al., J. of Immunol. Meth. 61:367-375 (1983).
A. Voller et al., The Enzyme Linked Immunosorbent Assay (ELISA).
P. M. Burrows et al., J. of Virol. Meth. 8:207-216 (1984).

*Primary Examiner*—Dale M. Shaw
*Assistant Examiner*—Laura Brutman
*Attorney, Agent, or Firm*—Finnegan, Henderson, Farabow, Garrett and Dunner

[57] ABSTRACT

A process is indicated for improving the accuracy and reproducibility of the data measured in immunometric tests which are carried out using microtitration plates and in which a pipetting drift is observed. Correction is made by pipetting in a test control in a multiple determination at the start and at the end of a series of samples for examination, and deriving, from the change in the values measured in this multiple determination, a correction factor, varying from the start to the end, for the intermediate samples under examination.

7 Claims, 5 Drawing Sheets

PROCESS FOR IMPROVING THE ACCURACY AND REPRODUCIBILITY OF DATA MEASURED IN IMMUNOMETRIC TESTS

The invention relates to a process for improving the accuracy and reproducibility of data measured in immunometric tests, particularly those carried out using microtitration plates.

When a sample for examination is employed in the test dilution prescribed for the particular immunometric test, it gives a measured number or value appropriate to the test. Without intending that the invention should be limited thereto, its essential characteristics will be described below by means of the enzyme linked immunosorbent assay (ELISA) as a typical example of the immunometric tests to which it can preferably be applied. In ELISA, measurement is evaluated via a photometer, the values measured being values of optical density (o.d.). A test set-up in which a stronger concentration of analyte gives a higher o.d. is taken as an example, i.e. the example is not a competitive test. However, this does not constitute any limitation of the invention either.

If the analyte detected in a sample under examination in ELISA is to be quantified, decisive importance attaches to the accuracy and the reproducibility of the individual measured value allocated to the sample. In this regard it is immaterial whether the analyte is, for example, an antigen or an antibody, or how the quantification is carried out.

Since the causes leading to a reduction in the accuracy and reproducibility of data measured in ELISA are very varied, a rough classification is helpful. This division makes it possible to illustrate the efforts which have already been made to achieve an improvement in accuracy and reproducibility of values measured in immunometric tests, in particular ELISA values.

There are no ideal conditions for evaluating the accuracy and reproducibility of ELISA tests. It is generally known that every kind of variable factor affecting use, such as the characteristic of the sample under examination, the batches of reagents, the form in which the reagents are made up, the technical equipment, the person carrying out the test and the time of carrying out the test etc., affects the result measured to a greater or lesser extent. These variables can falsify the value measured for the samples under investigation in the same way as for a control sample.

The accuracy of a measured value can only be checked on the basis of a standard measured value. As a rule this is carried out not on the samples under examination but on the test control included with the ELISA by the reagent manufacturer. For the starting material and for the establishment of the standard value for this test control, there are no exact instructions in which the attempt is made by suitable formation of a mean value to keep the deviations from the standard value as small as possible. An assessment of the Verband der Diagnostikaund Diagnostikagerate-Hersteller e.V. ("Association of Manufacturers of Diagnostics and Diagnostic Equipment") model for determining the standard value has been quoted by B. Muller-Wiegand et al., Lab. med. 10: 65–70 (1986).

In the case of the reproducibility of a measured value a distinction is drawn between within-run precision and between-run precision. The latter implies, for example, the precision from day to day or from one laboratory to another. The measurable value used both for within-run precision and for between-run precision is the variation coefficient VC %, where $$VC = \frac{\text{standard deviation}}{\text{mean value}} \cdot 100$$

Detailed statistical investigations and estimates of reproducibility have been given, for example, by M. J. Bookbinder and K. J. Panosian, Clin. chem. 32/9: 1734–1737 (1986), the within-run variation being compared with the between-run variation.

The within-run reproducibility is determined to a considerable extent by the quality of the reagents and the technical equipment. W. Ehnert, Lab. med. 3: A + B 75-76 (1979), discusses improvements in the determination of standard deviations within a run by means of multiple determinations. It is known that the precision can be improved by a duplicate determination of the samples under examination. However, duplicate determinations of the samples under investigation increase costs greatly and are therefore uneconomic.

Furthermore, a duplicate determination of samples under investigation in ELISA tests which are carried out on microtitration plates is of limited value if the second determination is carried out in an adjacent position, as shown, for example, from the investigations of B. W. Stemshorn et al., J. of Immunol. meth., 61: 367-375 (1983). It is more effective to carry out the second determination in an exactly prescribed set-up, at a distance from the first determination in the microtitration plate. However, this procedure is expensive and scarcely practicable for the test user.

The between-run reproducibility is affected by a large number of factors that can scarcely be defined. Correction for the value measured on the samples under examination is usually carried out by referring to the test control carried out at the same time. This test control gives a "day's value" which is determined in most cases as the mean value of a multiple determination. Comparing this current measured value with the standard value of the test control enables a correction factor to be determined by means of which the values measured on the samples under examination are each corrected in the same direction, as is described, for example, by A. Voller et al. in "The Enzyme Linked Immunosorbent Assay (ELISA)", A Guide with Abstracts of Microplate Applications, 1979. Thus, on the basis of the "day's value" of the test control, a deviation of the standard value of the test control applicable for the day is assumed, i.e. a trend which is regarded, at least partially, as also representative for the values measured on the samples under investigation ("level correction").

The correction for the values measured on the samples under examination is carried out by multiplying the values measured on the samples under examination by a factor equal to the factor of the deviation of the day's value of the test control from the standard value.

It is known that in the case of ELISA tests which are carried out in microtitration plates, the between-run reproducibility can be improved by changing the block arrangement of the samples under examination, as described by P. M. Burrows et al., J.Virol.Meth., 8:207–216 (1984). This procedure makes high demands on the person carrying out the test, is involved and has not been able to gain acceptance in industry for reasons of practicability.

In the course of investigations on ELISA tests on microtitration plates in order to improve interpretation of the values measured, the inventor of the present invention has now found that the deviation from the standard value alters within the series of samples on a microtitration plate. This deviation consists in the fact that a falsification of the measured values takes place in the opposite direction to the sequence in which the samples under examination are pipetted into the microtitration plate. This falsification can be demonstrated simply, by charging a microtitration plate solely with the positive test control, which is interpreted as a simulation of the sequence of the samples under examination.

Figure 1:
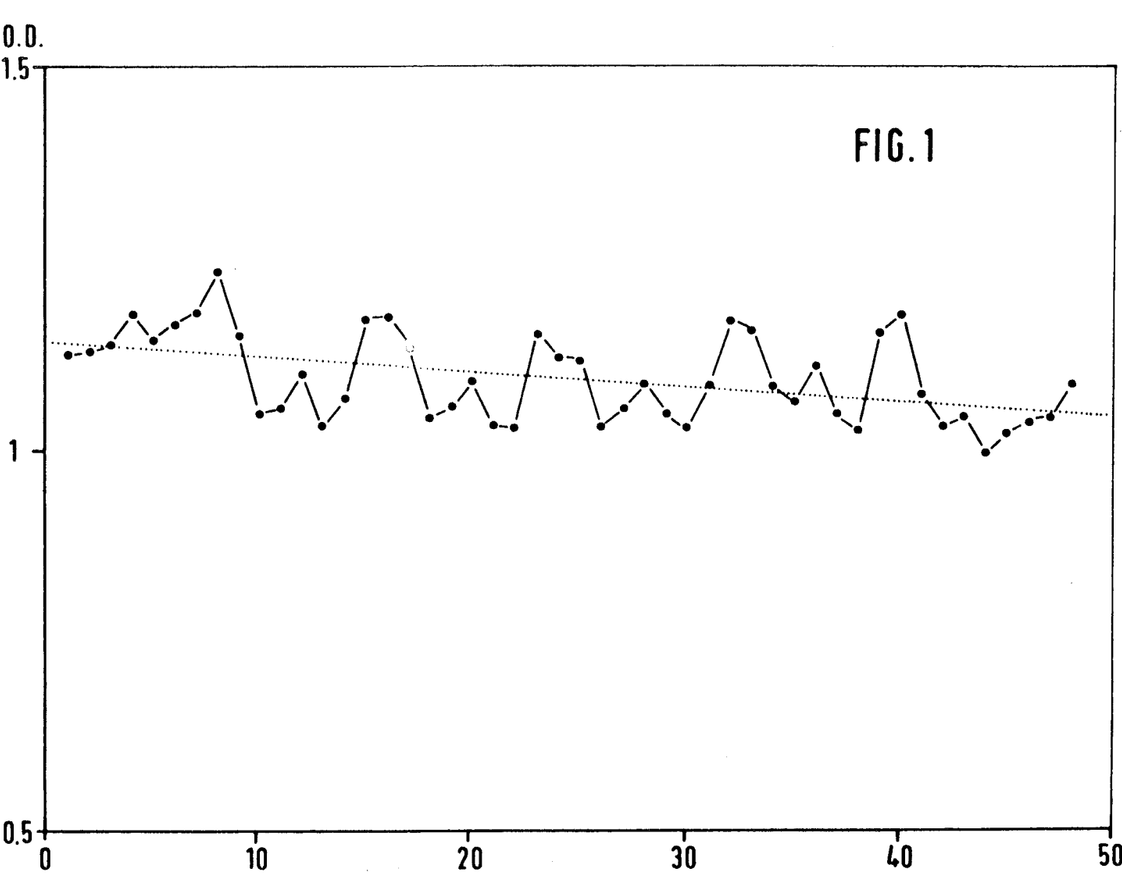
FIG. 1: Values of optical density o.d. measured as a function of the position within the pipetting sequence for a test control having a known standard value.

The results are shown in FIG. 1, the optical density o.d. being plotted in the graph as a function of the pipetting sequence.

The ELISA chosen for the examinations has a test for the detection of IgG antibodies against the German measles virus. The test set-up and the mode of functioning have been described in detail in European Patent Applications 0,264,866 and 0,270,729.

The measured values plotted in FIG. 1 on the test control (P/N 296), which alone was pipetted, show that the values measured at the start of the series are higher than at the end of the series. The test control employed has a standard value of 0.862. It can thus be seen, in addition, that even the last value in the series is still too high.

The cause of the effect observed, i.e. the "pipetting drift" observed, is that, even when the samples under examination are pipetted in normally at below room temperature, the analyte to be detected begins to bind onto the solid phase. The longer this unintended preliminary reaction, the greater the falsification of the measured value in question.

The observation that even the value measured in the last pipetting is higher than the standard value is based on a trend for all the values of this series (level) to increase.

The falsification of the values measured cause by "pipetting drift" always leads to a more or less pronounced increase in the value measured on a sample under examination, as a function of its position within the series.

In contrast to "pipetting drift", the daily trend of a series (level) is by definition the same for all the samples under examination and can falsify the individual measured values both upwards and downwards.

The intensity of the "pipetting drift" within a series depends on the room temperature, the temperature of the samples pipetted in, the temperature of the microtitration plate and the duration of time from the introduction of the first sample under examination up to the introduction of the last sample.

The "pipetting drift" also impairs the between-run reproducibility, because both of the marginal conditions mentioned previously, such as temperature and pipetting time, and also the positioning of the samples within the series can vary from day to day or from laboratory to laboratory.

The object of the invention is, therefore, to provide a process by means of which the "pipetting drift" described above can be corrected, without affecting, and in particular reducing, the effectiveness of existing correction procedures for a trend common to all the samples under examination ("level correction").

This object is achieved by means of a process such as is indicated in claim 1.

Further advantageous embodiments of the invention are indicated in claims 2 to 7.

Carrying out the process according to the invention requires first a positive test control of the customary type with an indication of a standard value prescribed for the particular ELISA. This test control is employed both within a run and also in the same manner between runs. The charging of the microtitration plates begins in each case with a multiple determination of the positive test control, is continued by pipetting in the samples under examination and ends with a further multiple determination of the same positive test control. For the purposes of this invention, duplicate determinations are in most cases adequate as multiple determinations. The sequence of the samples pipetted in must be laid down for the process of the invention within the geometry of the microtitration plate—for example horizontally or vertically.

After the test for one series has been carried out and the individual measured values are available, the mean values (or medians) of the appropriate multiple determinations of the positive test control at the start and at the end of the series are determined and are compared with one another, in order to appreciate the extent of the pipetting drift. If the mean value of the multiple determination at the start is numerically greater than that at the end, the existence of a "pipetting drift" is assumed.

It should be noted at this point that in immunometric tests in which there is a negative correlation between the concentration of the analyte to be detected and the numerical size of the measured value, as is the case in competitive tests, a pipetting drift, i.e. a systematic error, is assumed if the mean of the determinations on the test control is lower at the start of the run that at the end of the run.

The two mean values of the test control at the start and at the end are then compared with the standard value. In the case of a "pipetting drift" the mean value of the test control has a certain deviation from the standard value at the start of the series, but the mean value at the end has another deviation. A correction for measured values, for example by means of a correction factor, must therefore be different at the start of the series from that at the end of the series. In accordance with the invention, therefore, the correction for the measured value is altered as a function of the position of a sample within the pipetting sequence. For this purpose it is necessary to make assumptions on the systematic error caused by the pipetting drift.

In one embodiment of the invention a series, for example a series obtained from the manufacturer of the reagents, is carried out solely with a test control having a known standard value. The shape of the curve produced by the pipetting drift is then assumed to be the shape of the curve of the systematic error for subsequent measurements. This means that, if, in the case of measurements carried out on samples for examination, the mean values at the start and at the end of the series have been determined in accordance with the invention, it is assumed that the shape of the curve between these mean values conforms to a curve shape such as that found in the preliminary test on a test control. In mathematical terms, a theoretical curve is constructed by means of these mean values determined in actuality at the start and at the end, and the measured values for the individual samples under investigation are increased or reduced by an amount which, depending on its position within the pipetting sequence, is proportional to the deviation of the assumed correction curve for the test control sample from the initial or final value of the test control sample at the point corresponding to the same position.

In accordance with the invention, therefore, the correction for the samples under investigation between the multiple determinations of the test control within the series of positioned samples under investigation is carried out differently, depending on its position within similar will the correction factor be to the positive test control carried out at the start. The further back in the series the position of a sample under investigation, the more similar the correction factor to the factor of the positive test control at the end.

The correction to be altered in the direction of pipetting the samples under examination can determined mathematically in various ways. A simple correction, which is generally adequate in practice, is based on the assumption that the shape of the curve of the systematic error between the start and the end of the series is linear. In this case the appropriate correction factors can be calculated simply from the mean values of the positive test control by constructing a straight line having a negative gradient in the direction of sample input in accordance with the formula $$y = m \cdot i + b$$

If the optical density o.d. of the ith sample is called s(i), the o.d. of the test control measured at the start of the series is called s(1) and the o.d. of the test control measured at the end of the series is called s(n), the gradient m in the above formula is then obtained as $$m = \frac{s(n) - s(1)}{n - 1}$$

and the intercept of the axis is obtained as $$b = s(1) \frac{s(n) - s(1)}{n - 1}$$

This gives, for each sample under investigation, a correction factor $$k(i) = \frac{\text{standard value of the control}}{m \cdot i + b}$$

where i defines the position of the sample.

In practical applications of the invention a suitable computing program is set up for a computer which accepts the data measured on the microtitration plate by a photometer and automatically corrects them.

The advantages of the process according to the invention are demonstrated below by means of simulation tests and practical examples. Reference is made in this connection to the attached Figures and Tables.

The following are shown in the graphs.

The results measured in FIGS. 2 to 5 are evaluated numerically in Table 1.

TABLE 1

| Data from FIG. | Enzygnost-Anti-Rubella Virus/IgG IgG (POD) Comparison of P/N 296 uncorrected versus corrected | | | |
|---|---|---|---|---|
| | Accuracy* (standard value 0.862) | | Reproducibility** (VC) | |
| | before correction | after correction | before correction | after correction |
| 2 | 0.931 | 0.819 | 4.9% | 3.7% |
| 3 | 0.960 | 0.865 | 7.2% | 4.2% |
| 4 | 0.714 | 0.819 | 8.7% | 5.2% |
| 5 | 0.716 | 0.836 | 15.1% | 8.1% |

*mean value of 14 determinations in series
**within the series

FIG. 1 shows values of optical density measured on a test control having a known standard value in the ELISA test already mentioned above. The pipetting drift can be seen clearly. The shape of the curve has been assumed to be linear, as the dotted curve shows. The same test control was employed in accordance with the invention as a duplicate determination at the start and at the end in each case of a series which exactly filled a microtitration plate. In order to investigate the process according to the invention in practice, the same test control was then pipetted in alternately with samples under investigation from patients in a previously selected sequence (in this case vertical). No account was taken of the patients, samples for the curves shown in FIGS. 2 to 5; their only purpose was to simulate the practical conditions (time consumed, change of pipette tips etc.).

Figure 2:
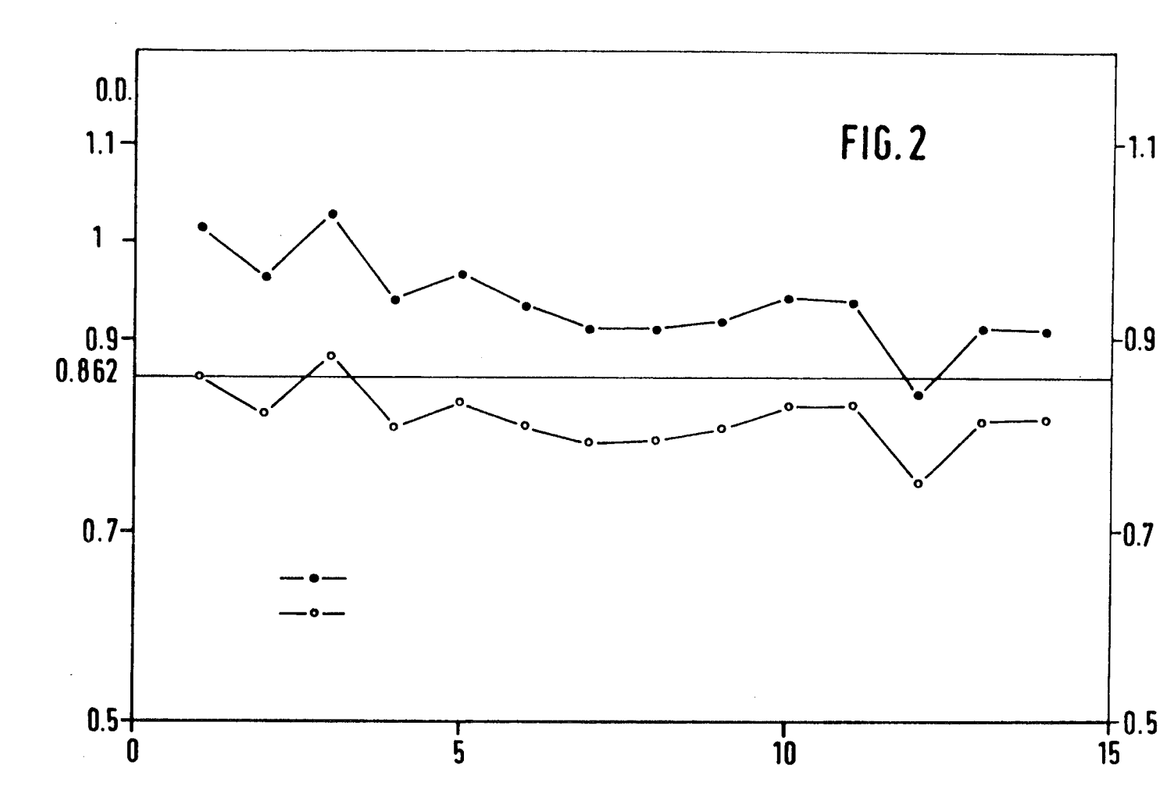
FIG. 2: Values of optical density o.d. measured as a function of the position within the pipetting sequence on samples under examination, as an uncorrected curve and as a curve corrected in accordance with the invention.

In FIG. 2 the measured values obtained for the test controls distributed within the series are shown before and after the correction according to the invention. The x-axis shows the pipetting sequence and the y-axis shows the value of optical density o.d. measured. The horizontal line plotted at an o.d. of 0.862 represents the standard value of the test control. The result of the duplicate determination of the test control at the start and end of the series has not been plotted.

In comparing the curve of the uncorrected values with the standard value it can readily be seen that all the values have too high a level. At the same time the systematic error caused by the pipetting drift is the more strongly pronounced as an additional falsification of the values the earlier the sample was pipetted in. The correction of measured values by the process according to the invention reduces both disadvantageous effects.

Figure 3:
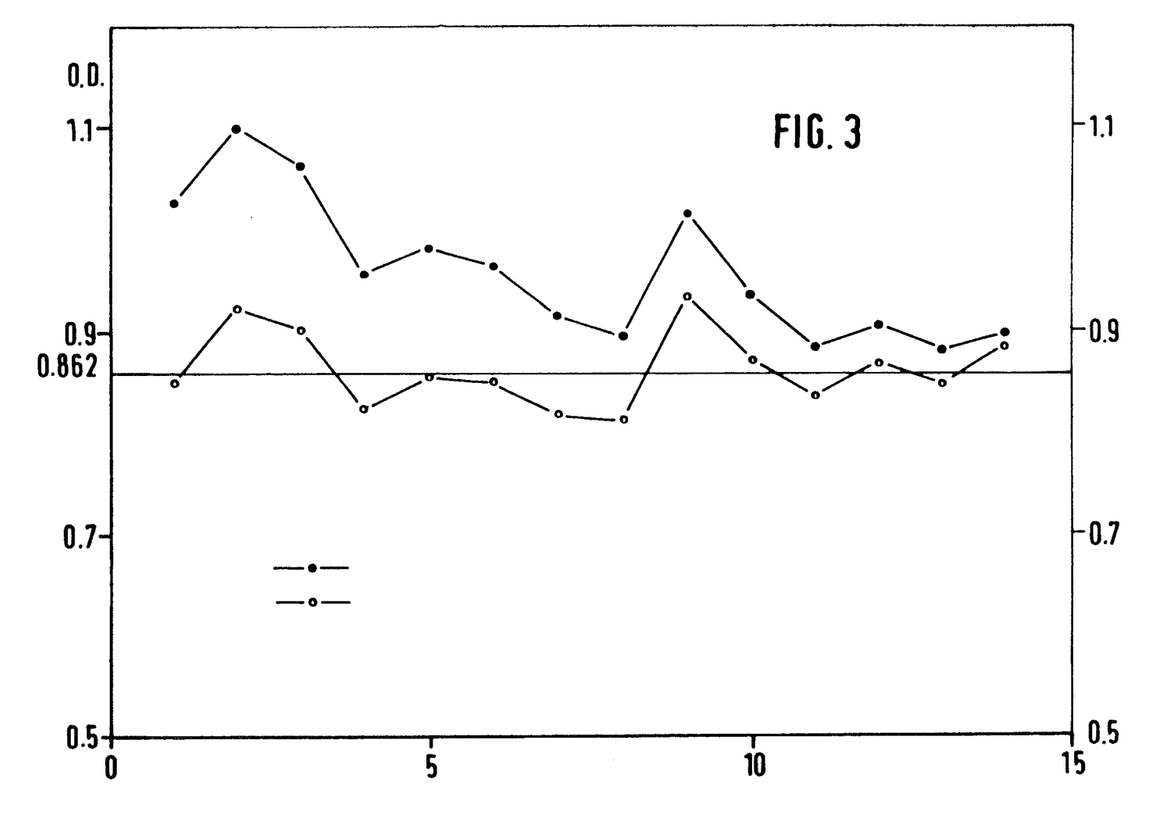
FIG. 3: A repetition of the series measurement forming the basis of the figure, carried out by the same test operator

The same person repeated the whole batch, giving a similar picture, as shown in FIG. 3. The pipetting drift was merely somewhat more strongly pronounced.

Correction by the process according to the invention gave an appreciable improvement in the accuracy of the values measured.

Figure 4:
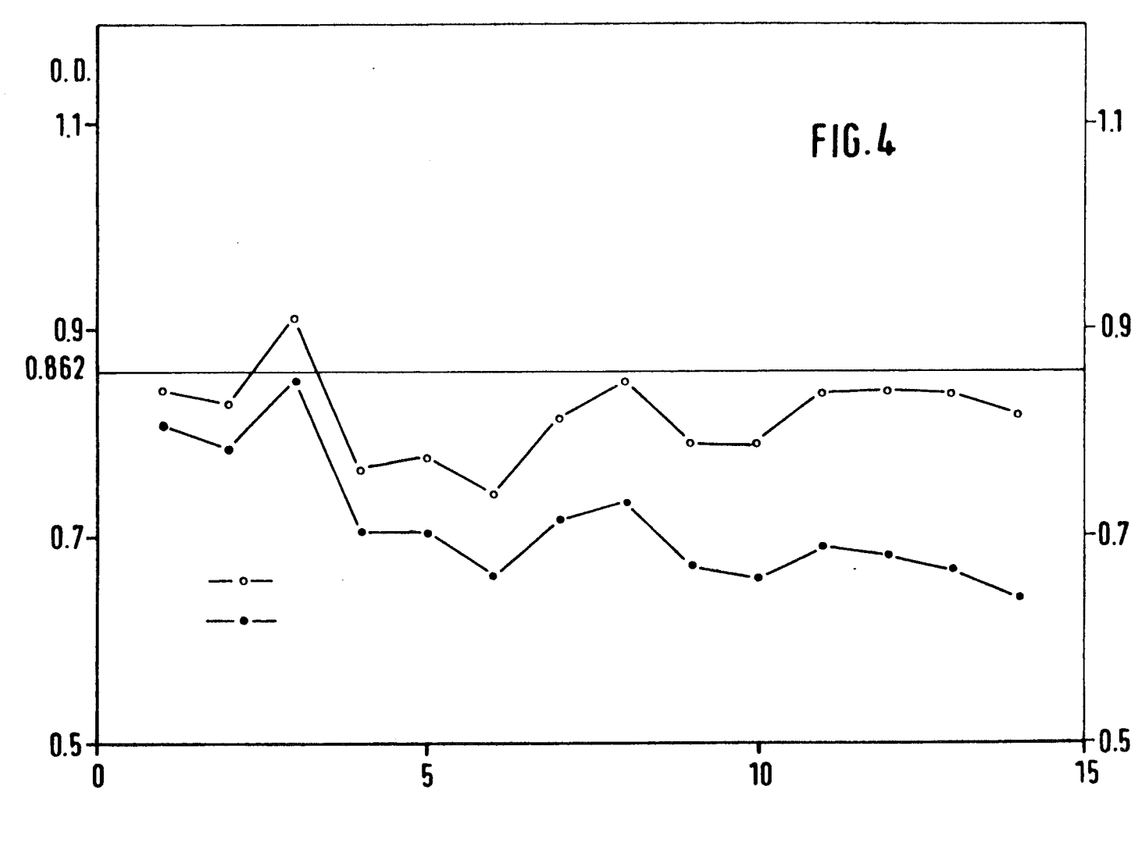
FIG. 4: A repetition of the series measurement forming the basis of the figure, carried out by another test operator

When another person carried out exactly the same batch of tests with the same reagents, a different shape of curve was obtained, which is shown in FIG. 4. Here the level of the uncorrected values was clearly too low, but at the same time a pipetting drift could be seen. Correction by the process according to the invention compensated for both the disadvantageous effects.

Figure 5:
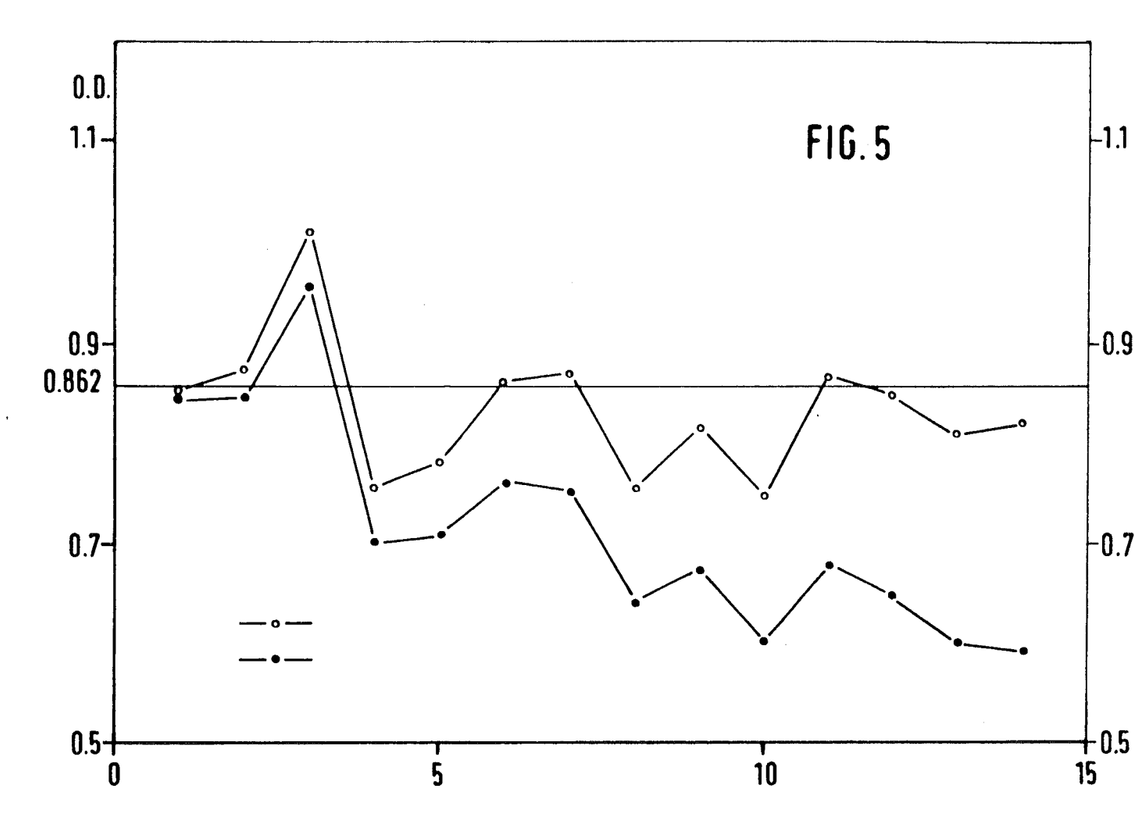
FIG. 5: A repetition of the series measurement forming the basis of the figure, carried out by the same test operator that carried out the series measurement for FIG. 4.

When this batch was repeated by this same person a curve of similar shape was also obtained, as shown in FIG. 5. The process according to the invention again improved the individual measured values quite markedly in relation to the standard value of 0.862.

In the tests described hitherto, the test control distributed within the series simulated the effect of the position of various samples under examination having an unknown content of antibodies against the German measles virus. This has the advantage that it is possible to compare not only the reproducibility, but also the accuracy of the measured values before and after the correction according to the invention. The corresponding values are shown in Table 1.

It is remarkable that the correction according to the invention acts independently of the particular level of the measured values. Irrespective of whether the series had too high a trend (FIGS. 2 and 3) or too low a trend (FIGS. 4 and 5), the pipetting drift was always corrected so that both the accuracy and the reproducibility of the measured values were improved.

Using this result as a basis, the experimental starting conditions for the process according to the invention were made more difficult in respect of several points:

1) patients' samples were examined, 2) the between-run reproducibility was tested, changing the positioning of the individual samples within the series, and 3) operations were carried out not only with the ELISA test described above for the detection of virus-specific IgG, but also, in addition, with a further test which detects the IgM against German measles virus. In the latter case the test control prescribed for this test variant, which has a standard value at an o.d. of 0.392, was employed.

The results are shown in Table 2 and once again indicate clearly that the process according to the invention also improves the reproducibility of values measured on samples taken from practice. The accuracy could not be evaluated, because these samples do not have a standard value.

Since a fairly large amount of data (altogether 9 samples having series lengths of n=10 to n=14) was available in these investigations, it is possible to make a rough estimate of the improvement in between-run reproducibility achieved by means of the process according to the invention. In the ELISA test used, the variation coefficient VC falls on average from 13.7% to 9.4%.

TABLE 2

COMPARISON OF PATIENT SAMPLES UNCORRECTED VERSUS CORRECTED

| Sample identification | Between-run reproducibility | | | | | |
|---|---|---|---|---|---|---|
| | before correction | | | after correction | | |
| | n | x̄ | Vk | n | x̄ | Vk |
| ENZYGNOST-ANTI-RUBELLA VIRUS/IgG (POD) | | | | | | |
| 068810 | 12 | 1.267 | 13.5% | 12 | 1.338 | 10.0% |
| 7/190 | 12 | 1.314 | 16.7% | 12 | 1.390 | 7.5% |
| Pool VII | 12 | 2.333 | 8.3% | 12 | 2.468 | 5.7% |
| ENZYGNOST-ANTI-RUBELLA VIRUS/IgM (POD) | | | | | | |
| 411818 | 14 | 0.425 | 17.4% | 14 | 0.400 | 11.3% |
| 242 | 14 | 0.384 | 17.0% | 14 | 0.361 | 13.6% |
| 249 | 14 | 0.472 | 15.1% | 14 | 0.428 | 9.5% |
| 6528 | 10 | 0.385 | 13.4% | 10 | 0.337 | 9.5% |
| 263 | 14 | 1.051 | 11.4% | 14 | 0.988 | 10.1% |
| Pool VII | 14 | 0.782 | 10.5% | 14 | 0.735 | 7.8% |
| Estimated improvement: | | | Σ13.7% | | | Σ9.4% |

We claim:

1. An improved method for the immunometric detection and determination of an analyte of unknown concentration in a sample comprising the steps of:
   (A) fixing an immunological partner of said analyte to a solid-phase support;
   (B) adding a sample thought to contain said analyte to the solid-phase support;
   (C) allowing analyte within the sample to bind to the immunological partner;
   (D) determining a value for the amount of analyte bound; and
   (E) applying a correction factor to said value which is determined by further steps comprising:
      (1) performing steps (A), (B), (C) and (D) with at least one first standard sample which contains a known concentration of analyte before any other samples are tested;
      (2) performing steps (A), (B), (C) and (D) with at least one second standard sample of the same analyte concentration as the first, after all other samples have been tested; and
      (3) computing a correction factor for each sample of unknown analyte concentration tested based on the change in the mean values of the amount of analyte bound from said standard samples determined in steps (1) and (2).

2. The method as claimed in claim 1, wherein samples are sequentially numbered according to the pipetting order from i=1 to i=total number of samples (n), wherein at least two samples are used as standards in steps (1) and (2), and wherein said correction factor, k(i), is a function of the mean value of the values of the amount of analyte determined to be bound in steps (1) and (2) where:

s(1) = average initial value of the standard samples;
s(n) = average initial value of the standard samples;
m = /(n − 1);
b = s(1); and
k(i) = standard value of the control/m(i + b).

3. The method as claimed in claim 1, wherein each individual correction factor is derived from a function of the change in the mean value of the values measured for the amount of analyte bound from a sequential series of standard samples, with the shape of the resulting correction curve determined by experimental tests of the standard sample series, and increasing or reducing the values measured for the individual test samples by the correction factor which is directly proportional, depending on its sequential position (i), to the deviation of the individual standard sample tested from the correction curve.

4. The method as claimed in claim 1, wherein a systematic error is assumed in the case of immunometric tests in which there is a positive correlation between the concentration of the analyte to be determined and the numerical magnitude of the value measured, said error being corrected if the mean value of the values measured for the standard sample is greater at the start of the series rather than at the end of the series.

5. The method as claimed in claim 1, wherein a systematic error is assumed in the case of immunometric tests in which there is a negative correlation between the concentration of the analyte to be determined and the numerical magnitude of the value measured, said error being corrected if the mean value of the values measured for the standard sample is greater at the start of the series rather than at the end of the series.

6. The method as claimed in claim 1, wherein the shape of the curve is step-wise, each step representing the change in the mean value of the values measured for the standard samples, and the number of steps corresponding to the number of test samples.

7. The method as claimed in claim 1, wherein the correction factors obtained with respect to systematic error caused by pipetting drift are further subjected to correction for a systematic error which falsifies all the samples under examination to the same extent.

* * * * *

UNITED STATES PATENT AND TRADEMARK OFFICE
CERTIFICATE OF CORRECTION

PATENT NO. : 5,138,551
DATED : August 11, 1992
INVENTOR(S) : HANS-DETLEF DOPATKA ET AL.

It is certified that error appears in the above-identified patent and that said Letters Patent is hereby corrected as shown below:

Column 8, line 57, should read: $m = \dfrac{s(n) - s(1)}{(n - 1)}$

Column 8, line 58, should read: $b = s(1) \dfrac{s(n) - s(1)}{(n - 1)}$

Signed and Sealed this

Fifth Day of October, 1993

Attest:

BRUCE LEHMAN

*Attesting Officer*  *Commissioner of Patents and Trademarks*